(12) United States Patent
Agrawal

(10) Patent No.: US 8,231,049 B2
(45) Date of Patent: Jul. 31, 2012

(54) METHOD OF AND APPARATUS FOR FORECASTING CASH DEMAND AND LOAD SCHEDULES FOR MONEY DISPENSERS

(76) Inventor: Subhash C. Agrawal, Boxboro, MA (US)

( * ) Notice: Subject to any disclaimer, the term of this patent is extended or adjusted under 35 U.S.C. 154(b) by 0 days.

(21) Appl. No.: 13/111,989

(22) Filed: May 20, 2011

(65) Prior Publication Data

US 2011/0225087 A1   Sep. 15, 2011

Related U.S. Application Data

(62) Division of application No. 11/157,238, filed on Jun. 21, 2005, now Pat. No. 7,946,474.

(60) Provisional application No. 60/581,533, filed on Jun. 21, 2004.

(51) Int. Cl.
*G06F 17/00* (2006.01)

(52) U.S. Cl. ........ 235/376; 235/379; 235/380; 235/493; 705/43; 705/44

(58) Field of Classification Search .................. 235/376, 235/379, 381, 493; 705/43, 44
See application file for complete search history.

(56) References Cited

U.S. PATENT DOCUMENTS

| 7,545,816 B1 * | 6/2009 | Coutts et al. ................. 370/400 |
| 2004/0215566 A1 * | 10/2004 | Meurer .......................... 705/43 |

* cited by examiner

*Primary Examiner* — Allyson Trail
(74) *Attorney, Agent, or Firm* — David H. Judson

(57) ABSTRACT

A method of and apparatus for forecasting cash demand for an automated teller machine (ATM) or any other cash dispensing devices for individual days, weeks and multi-day load periods. In one embodiment, an expected value of withdrawal for any particular period, as well as an upper limit on expected withdrawals for a given confidence level, are computed. The invention facilitates the creation of a daily and multi-day withdrawal forecast for a given ATM. The forecasts are also used to compute an optimum load amount for a given load period (the period between loading operations) for a given ATM, subject to given parameters (such as courier cost, interest rate, transit time, desired confidence level, cost of run-out, and the like) and given constraints (bundle size, maximum capacity, possible delivery days, and the like). The forecasts are also used to determine an optimal load period length and schedule. After the ATM is loaded, the system monitors cash in the ATM during a load period to facilitate potential corrective action if actual withdrawals exceed forecasted withdrawals or, in the alternative, if the ATM will contain excessive funds on its upcoming regularly scheduled load date, e.g., due to much lower withdrawals than expected or due to the ATM becoming unavailable for a given portion of the load period.

9 Claims, 4 Drawing Sheets

METHOD OF AND APPARATUS FOR FORECASTING CASH DEMAND AND LOAD SCHEDULES FOR MONEY DISPENSERS

This application is a division of Ser. No. 11/157,238, filed Jun. 21, 2005, now U.S. Pat. No. 7,946,474, which application was based on Ser. No. 60/581,533, filed Jun. 21, 2004.

BACKGROUND OF THE INVENTION

In the financial industry, automated teller machines (ATMs) are an important means of providing quality customer service. ATMs provide customers a convenient way to transact bank business while saving time. Accordingly, financial institutions have significant incentive to ensure that their ATMs are continuously available and functioning correctly.

ATM management services are well-known in the art and include, among others, cash replenishment, computerized monitoring system, full first-line maintenance (including replacement of all consumables, screen software uploads and emergency call-outs) and computer video link monitoring. ATM software products are also widely available and include cash management predicting functions. One such product is ATM Manager Pro, available from e-Classic Systems, Inc. This product enables a financial institution to forecast cash out dates and to propose appropriate replenishment amounts, to generate cash orders and loads, to balance vault cash and other cash accounts, and to reconcile settlement details by terminal or by date. In ATM Manager Pro, a model of a withdrawal pattern is generated for a particular machine and then averaged over a given time period (e.g., 28 days) to create a "per day" average for the period. In addition to these known products and services, the patent literature also describes techniques for ATM management such as computer-implemented cash flow predictive algorithms. One such technique is described in U.S. Pat. No. 5,799,288 to Tanaka et al. This patent describes a money management system to predict and manage a demanded cash amount for an ATM. In particular, the system cumulatively stores transaction data from an ATM and uses that data to develop a model of the withdrawal pattern. That model uses data for one (1) year from a number of sources and calculates weights for a number of qualitative factors. A prediction algorithm calculates and predicts demanded cash amounts within a designated time for the machine based on the model.

These and other known approaches provide useful information to the financial institution or other ATM service provider, but their cash demand forecasts are relatively simple and do not take into consideration true machine use situations or the particular ATM's operating environment. Thus, for example, a financial institution might expect a withdrawal pattern on Fridays to be somewhat similar over a given month but perhaps very different from the withdrawal pattern on Wednesdays, as Fridays are often pay days or days in which users withdraw money for weekends. Depending upon the location of the ATM, withdrawals also may be affected by season, e.g., ATMs located in ski areas experience higher demand in winter and lower demand in the summer; conversely, ATMs located in towns near beaches experience higher demand in summer and lower demand in winter. An institution may also experience unexpected demand from a given machine in close proximity to a venue at which a given concert or special event is taking place. Prior art cash demand forecasting techniques are often based upon rules of thumb, relying upon experienced operators, and they are not robust enough to provide meaningful forecasts for these and other "real-world" situations. As a result, ATMs are often loaded with extra funds, reducing the profits of the ATM operator, or they are loaded with not enough funds, resulting into unsatisfied customers and lost revenue for the ATM operator.

The present invention addresses the long felt need in the art for improved techniques for forecasting cash demand and load schedules for automated teller machines.

BRIEF SUMMARY OF THE INVENTION

It is an object of the invention to provide a method of and apparatus for forecasting cash demand for an automated teller machine (ATM) or any other cash dispensing devices for individual days, weeks and multi-day load periods. In one embodiment, an expected value of withdrawal for any particular period, as well as an upper limit on expected withdrawals for a given confidence level, are computed. The invention facilitates the creation of a daily and multi-day withdrawal forecast for a given ATM.

It is a further object of the invention to describe techniques for using such forecasts to compute an optimum load amount for a given load period for a given ATM, subject to given parameters (such as courier cost, interest rate, transit time, desired confidence level, and the like) and given constraints (bundle size, maximum capacity, possible delivery days, and the like).

It is still another more general object of the invention to determine an optimum period between loads in an ATM given desired confidence levels and certain criteria, e.g., that money put into the ATM is going to be sufficient for anticipated demand, the cost of the ATM running out of money as lost revenue, and a cost of doing emergency loads.

Another more particular object of the invention is to provide an ATM cash demand and load scheduling system that monitors cash in an ATM during a load period (the period between loading operations) and that facilitates potential corrective action because actual withdrawals exceed forecasted withdrawals or, in the alternative, because the ATM contains excessive funds on its upcoming regularly scheduled load date, e.g., due to much lower withdrawals than expected, or due to the ATM becoming unavailable (for dispensing money) for a given portion of the load period.

The present invention also enables an ATM system operator to answer necessary "what-if" questions and to optimize its operations taking into account variables affecting operation. Examples of such variables include, without limitation, the constraints on when machines can be loaded, machine capacity for holding cash in different denominations, acceptable likelihood of cash being run out, interest rates, money transit times, cost of loading cash, and the like. In a representative embodiment, the invention is a self-learning system that automatically configures itself from the withdrawal data for each ATM separately.

In an illustrative embodiment, a computer implemented ATM cash forecasting and load scheduling system preferably has a number of components: data clean up to address exception conditions, model building, forecasting, optimization, and monitoring. Each of these high level components may be implemented in software executable in given commodity hardware having an operating system.

Preferably, the forecasting and load scheduling system operates on a "per ATM" (or, more generally, per machine) basis. It can also operate on a per site basis, where a site is defined as being a collection of ATMs that are at the same location and placed such that, if one ATM is out of funds, the customer can use another machine very conveniently so that no revenue is lost to the service provider. In an illustrative embodiment, a model building component preferably operates by separating incoming cash withdrawal data (e.g., a data stream provided by a data collector) by day of the week, e.g., Tuesday, Saturday, and the like. The data for a given day optionally is then "corrected" (i.e. adjusted or modified) to address one or more "special" situations or anomalies, such as machine breakdown, the existence of a given event that might cause short-term ATM "flash" crowds, and the like. After this "day of the week" data is adjusted for "special" situations or anomalies, the modeling component preferably builds cash demand (withdrawal) models that are used to generate load data (load period, load schedule, load amount) for the given ATM. The modeling component preferably operates as follows. For each day of the week (e.g., a Thursday), the component builds a model of withdrawals for that day of the week, using a data series consisting of historical cash withdrawals on that day of the week. This model preferably is built by fitting a mathematical function containing non-periodic (linear and non-linear) components as well as periodic components, to the historical withdrawal data. This function fitting can be done using standard non-linear regression analysis in a single step, or in multiple steps. After computing the parameters of the modeling function, preferably the modeling component determines the amount of random variation in the historical withdrawal that is not explained by the mathematical function fitted to the data. Thus, for a given day of the week, the modeling component computes parameters of a modeling function, and an unexplained random variation.

For each calendar date, and given a desired confidence level and the forecasting model for the day of the week for that date, the invention generates a forecast of expected cash withdrawals. The forecast preferably includes:

expected value of the money to be withdrawn, and an "upper limit value" such that the likelihood that the withdrawals will be less than or equal to the upper limit is given the "confidence level."

The forecast of expected withdrawals typically is based on the modeling function for the day of the week and the unexplained random variation for the day of the week. This forecast for the date preferably is then corrected for expected special situations not already taken into account by the modeling function.

In like manner, a forecast for a multi-day period may be created, preferably by aggregating forecasts for each of the dates in the period; in such case, forecasts for each date are computed, as before, using the models for the corresponding days of the week. For a given ATM, given load period and confidence level, the upper limit on the amount of money expected to be withdrawn during this multi-day load period then is the amount of money that is recommended to be loaded in the ATM. (A load period is defined by the date on which the ATM will be loaded with additional money and the length of the load period, i.e., the number of days until the date of next load.)

A load schedule optimizing component computes optimum load schedule and, in particular, optimum load period length. In particular, for each potential size multi-day load period beginning with a projected load date, preferably the module computes a total cost of money based on the forecasted daily withdrawals (and upper limits on total withdrawals), preferably taking into consideration given cost parameters (e.g., courier cost, interest rate, money transit time, bundle size, and the like). Then, the component computes an optimum number of days between loads, minimizing a unit cost of loading money into the ATM by taking into account money delivery or scheduling constraints, and a maximum capacity of the ATM.

The monitoring component preferably operates during a current load period as new data becomes available on actual withdrawals. The component compares the actual withdrawals against the forecasted withdrawals. Using the old forecast of withdrawals for the future days, differences between actual withdrawals and the forecasts for the days already past in the current load period, as well as the actual funds that remain available in the machine, the component computes a projected ATM "run out" date and a forecast of residual amounts on the expected next load date. The component then performs (or recommends performance of) necessary or desirable funding corrections for the machine.

The foregoing has outlined some of the more pertinent features of the invention. These features should be construed to be merely illustrative. Many other beneficial results can be attained by applying the disclosed invention in a different manner or by modifying the invention as will be described.

DETAILED DESCRIPTION OF AN ILLUSTRATIVE EMBODIMENT

Glossary

Figure 1:
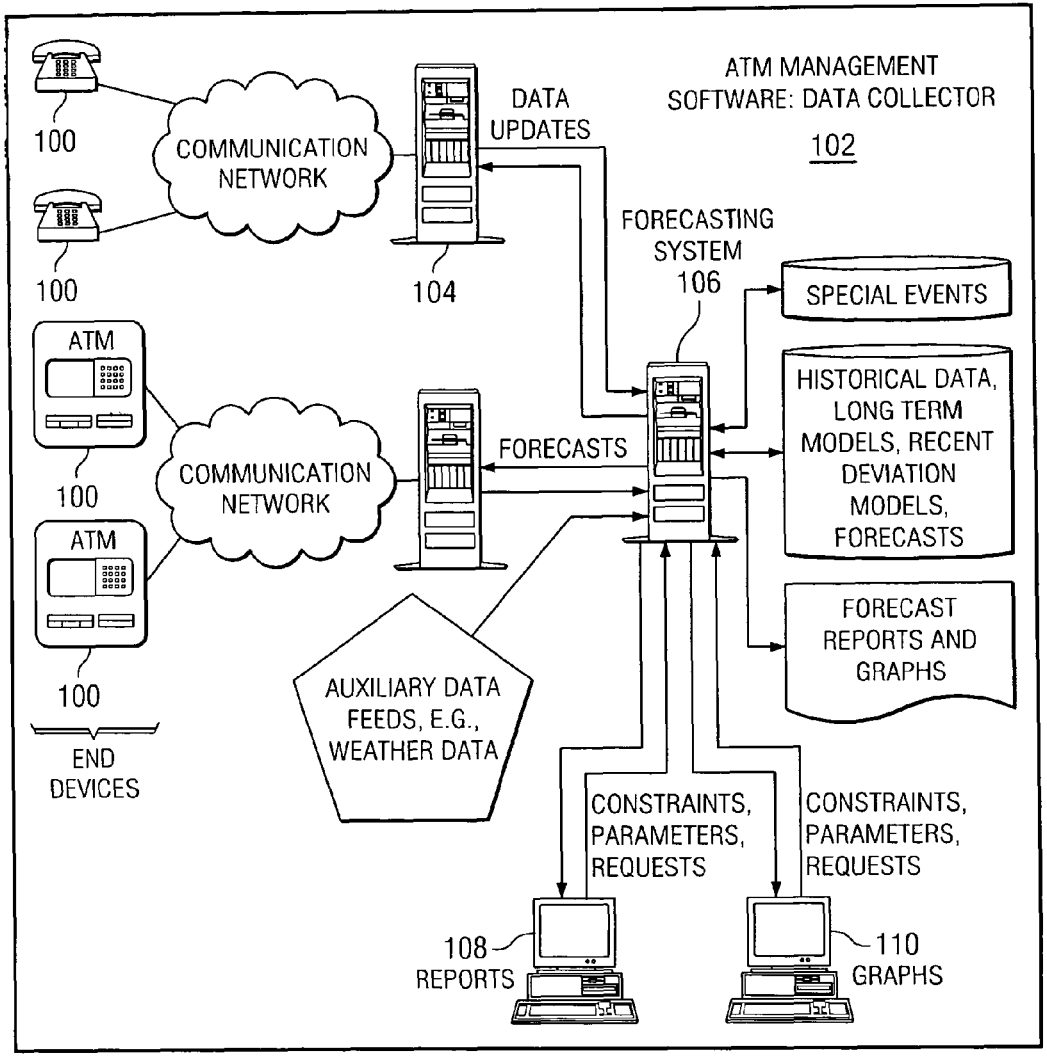
FIG. 1 is a simplified block diagram illustrating a distributed environment in which the present invention may be implemented.

The following are definitions for various terms that are used in the descriptive text that follows:

date: generally refers to calendar date; however, when "date" is used as an argument or input to a mathematical function, the calendar date preferably is translated into a number of days since a reference date, e.g., assuming Jan. 1, 2000 as a reference date, Jan. 1, 2004 is translated into 1461 (days since Jan. 1, 2000);

load date: date on which an ATM (or other dispenser) is loaded with new funds or items being dispensed, as the case may be;

load period: a time period between one load (date) and the next load (date); a time between a first load of a given machine and a next load of the given machine is sometimes referred to herein as a "load period";

load period length: a number of days between two consecutive load dates;

load amount: an mount of money that should be put in a given ATM;

residual: an amount of money left in a given ATM at the end of a load period; often, upon a next load the residual is removed and replaced with new funds;

add/swap: a load time option; when loading a given ATM, removal of all remaining (residual) money before reloading is a swap; otherwise, it is an add;

capacity: a maximum amount of money that a given ATM or a money dispenser may hold; the value is usually specified in terms of an amount of money (e.g., $) that, in turn, is derived from a bill thickness, stack height and a bill denomination; for machines that can dispense cash in multiple denominations, the capacity may be different for each denomination;

daily withdrawal: an amount of money (or other denomination, such as stamps) withdrawn on a particular date, also referred to as a data element (see below).

data element: a tuple (time, value, value type), e.g., an amount of total money withdrawn on the date, amount of money withdrawn in given $ bill denominations on the date, the number of stamps withdrawn on date, or the like;

overall data series or data series: a series of data elements for all observations during an entire historical period, irrespective of the day of the week;

data series by day of the week: a series of data elements for selected observations for a same day of the week (e.g., Monday) during a historical period;

model: a set of functions and other quantities that describe a withdrawal pattern associated with a given ATM; a model may have several components including a predictable component (as defined by a modeling function) and an unexplained or random variation component.

modeling function: a mathematical function or method representing a predictable component of withdrawals (for a specific day of the week, a specific ATM, or the like); the function may have several components, such as periodic components and non-periodic components;

unexplained or random variation: standard deviation of the difference between actual withdrawal and value computed by the modeling function for dates in the historical data series for that model; typically computed as a result of the regression;

model for a date: a model corresponding to the particular day that corresponds to the day of the week for that date;

periodic: shall mean having repeated cycles;

non-periodic: shall mean not having repeated cycles;

linear change: refers to when different points fall on a straight line;

non-linear change: refers to when different points do not fall on a straight line; the change may be periodic or non-periodic;

simple periodic function: a continuous function of given amplitude (a), period (p) (1/frequency) and phase shift (ph), e.g., a sine function such as $a*\sin(2*\pi*date/pd-ph)$; note that a cosine function also is a simple periodic function, as it is essentially a sine function shifted by 90 degrees or $\pi/2$ radians; further, in actual implementation, the date variable in the above sine function is taken as number of days since some reference date;

compound periodic function: a periodic function that is a combination of simple periodic functions; the component functions can have different periods or phases, e.g., A four component periodic function, where each component is a simple periodic function with independent period and phase:

$$a1*\sin(2*\pi*date/pd1-ph1)+a2*\sin(2*\pi*date/pd2-ph2)$$

$$+a3*\sin(2*\pi*date/pd3-ph3)+a4*\sin(2*\pi*date/pd4-ph4)$$

forecast for a date (some times also referred to as daily forecast): a forecast of the amount of money expected to be withdrawn from an ATM on the date; this forecast typically has two components:
expected value of the money to be withdrawn on the date, and
an "upper limit value" such that the likelihood of withdrawals on that date are less than or equal to the upper limit is given "confidence level".
forecast for a period: a forecast of the amount of money expected to be withdrawn from an ATM on the period. It has two components:
Expected value of the money to be withdrawn during the period, and
An "upper limit value" such that the likelihood of withdrawals during that period are less than or equal to the upper limit is given a "confidence level"
(desired) confidence level in a forecast: a (desired) likelihood of withdrawals during that period are less than or equal to the upper limit component of the forecast (specified amount);
forecasted residual: a forecast of the amount of money expected to be remaining in the ATM at the end of current load period; the forecasted residual also has two components
expected value
lower limit on forecasted residual.

Context Overview

FIG. 1 illustrates an overall context in which the invention may be implemented. End users withdraw money from ATMs 100 at random points. An ATM maintains information about the withdrawals. ATM management software 102, such as ATM Manager Pro™ from eClassic Systems, Inc., periodically collects this data at a data collector 104. This software periodically sends consolidated withdrawal information to a forecasting system 106, which implements the model building, forecasting, optimization and monitoring functions that were described generally above. Such data may be provided as a stream, in batch form, or in any other convenient manner. Generally, the forecasting system 106 records the withdrawal information, processes it, builds withdrawal models, determines when an ATM may run out of money, and determines the amount of next load and when the next load should be made, preferably taking into account a number of parameters including pre-existing load schedule and withdrawal patterns as will be described below. The forecasting system 106 also prepares and presents a number of reports 108 and graphs 110 for viewing by analysts and operators. The forecasting system 106 also allows the analysts to ask a number of "what if" questions to optimize the operations. Information exchange between different modules can be done in a number of different ways, e.g., a data collector can send the information to the forecasting system or the latter can ask for the information from a data collector. The devices can be operated over any convenient network, e.g., the Internet, a local area network, a dedicated private network, or the like. Communications between devices may rely upon well-known transport protocols.

Creating Withdrawal Data Series for Each Day of Week

In the case of ATMs, typically the incoming data is an amount (total cash withdrawals) on a given date. As data is collected over a given time period, the incoming data may be considered to be a "series" (i.e., a number of objects arranged or coming one after the other in succession). Over a given time period, incoming data may be treated as one data series, where withdrawal on each date represents a sample of a random variable. This random variable has a probability distribution function (PDF), and this PDF is a function of a number of parameters. Typically, however, there are significant intrinsic differences in the withdrawal patterns for a given ATM on different days of the week. For example, the withdrawal pattern on Fridays during a given month or season may be somewhat similar but very different from the withdrawal pattern on Wednesdays because Fridays are often pay days or days in which users withdraw money for weekends. The forecasting system 106 of the present invention addresses this and other real-world considerations, as will be seen.

Figure 2:
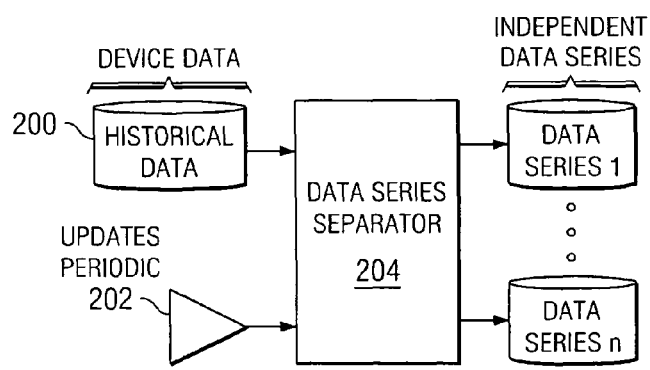
FIG. 2 illustrates a process of separating incoming data into an independent data series, one for each day of the week, according to a first feature of the present invention.

According to the invention, in an illustrative embodiment, as mentioned earlier, historical withdrawal data is divided into separate datasets or data series by day of the week, i.e., separate datasets for Monday, Tuesday, and so on and so forth; the entire dataset may be considered an aggregation of these separate datasets. As a generalization, according to the invention, preferably the incoming data series is processed and treated as an aggregate of a number of independent data series. FIG. 2 shows the process of separating incoming data (presumably received into the system on a daily basis over some time period) into independent data series according to this technique. In this example, historical data 200 for the given ATM and any periodic update data 202 is supplied to a data series separator function 204, which generates independent data series DS1 . . . DSn. The data series separator function 204 is implemented as a program, process, an execution thread, or the like and simply parses the incoming data into the separate buckets. Thus, in the illustrative embodiment, DS1 represents the data series for Mondays, DS2 represents the data series for Tuesdays, and so forth.

Cleaning Observed Data/Improving Quality of Raw Data for Modeling

An institution might expect the withdrawals on a specific date, a data element, to fit a given pattern or model for the day of the week corresponding to the date (i.e., the withdrawal for the date is a sample of the corresponding random variable for the day). This is not always the case, however, as there can be any number of situations that cause this assumption to be untrue. Examples of such situations include, without limitation, the ATM breaking down (and thus having relatively low withdrawals), the ATM facility being closed due to a holiday, a special event in the neighborhood, e.g., a concert or a game near the location where the ATM is located, and so forth. Thus, according to the invention, it is desirable to analyze the incoming data elements against a number of criteria to determine whether the observed data is an outlier as a result of conditions like the ones mentioned above. These criteria include, without limitation, historical statistics of withdrawal for the day of the week, any previous forecast of the withdrawal done at the load time, any special event specification for that date for the ATM, and any thresholds for determining special and exception situations. Some examples, without limitations, of the tests that can be performed to make such a determination are:

If (observed value>(historical mean withdrawal for the day of the week+3*standard deviation of the withdrawal for the week)) then {withdrawals for that date were probably exceptionally high}, If (observed value<(historical mean withdrawal for the day of the week) and (the balance at the end of the day was=0)) then {the ATM ran out that day}, If (observed value<(historical mean withdrawal for the day of the week−2*standard deviation of the withdrawal for the week)) and (the balance at the end of the day was>0)) then {either the withdrawals for that day were exceptionally low for that date or the machine broke down}.

Note that these tests are merely representative, and there is no requirement the withdrawal data be "corrected" with respect to all of these criteria, or any of them.

In an illustrative embodiment, it is desirable to determine if an exception has occurred on the date (e.g., ATM ran out or broke down) or if the date is a potential candidate for being an unanticipated or unspecified special event. If there is no potential exception or special situation, then preferably the data element (the data received for the date in question) is placed in the processed data series. When a potential exception situation or special event is identified, corrective action is taken on the observed value to improve the quality of the data series, and optionally appropriate messages are provided to enable the operator. Corrective actions include, for example, substituting the measured value (for the date in question) by an historical average or data from a previous forecast, eliminating from the data series the data for this date (the observed value being evaluated), or the like. Upon receiving the notification messages, operators can review and optionally define additional past or present special events, which may then be added to those already in the database.

Figure 3:
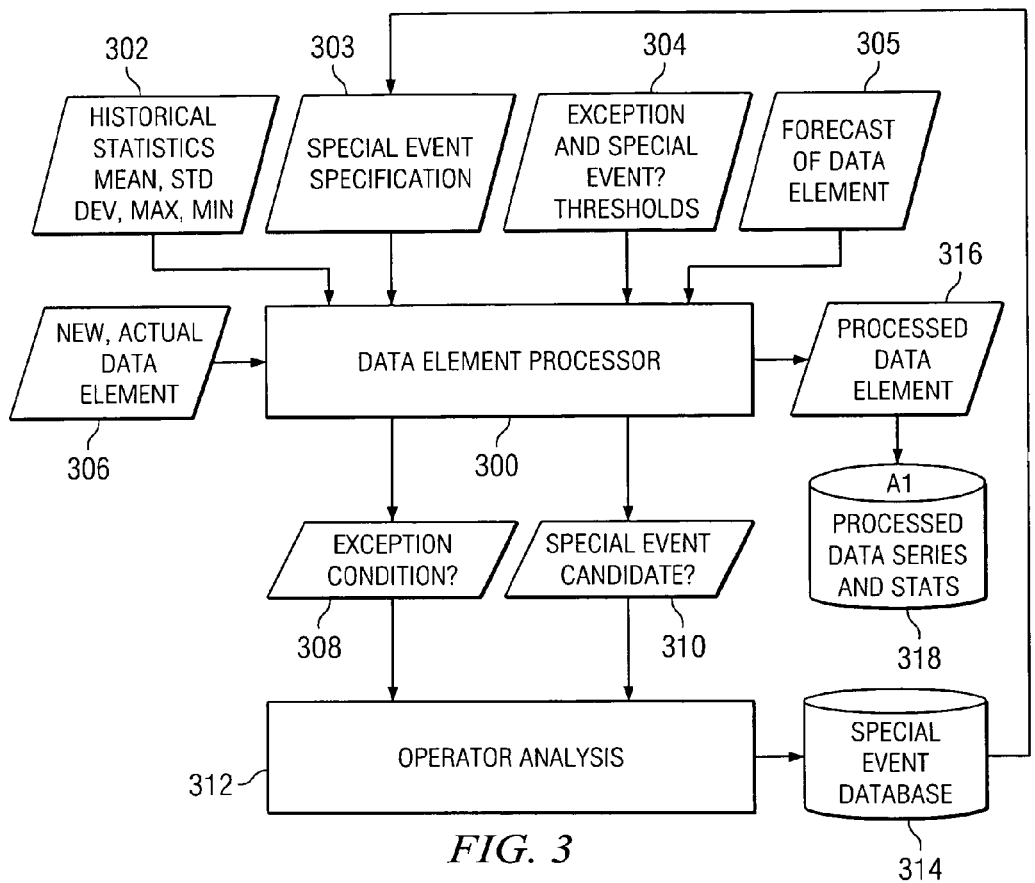
FIG. 3 illustrates how a data element in a data series may be processed according to one embodiment of the present invention.

Such data handling is illustrated in FIG. 3 and utilizes a data element processing function (a "data element processor") 300. As described above, this function is implemented in software executable on the computer. The data element processor preferably receives, as one or more inputs: historical statistics 302 (including mean, standard deviation, maximum and minimum), any exception and special event data 304 that has previously triggered a threshold, a special event specification 303 that defines a set of one or more special events that have been specified by the operator, and a forecast 305 for the date corresponding to the observed data element. For an input data element (labeled new, actual data element) 306, the data element processor 300 tests to determine whether an exception condition has been met at 308 or whether the data element represents a special event candidate at 310. If so, the data element is not put in the processed data series, and instead, operator is or may be notified to perform an appropriate analysis at 312. Thus, for example, the operator may determine to include the new data element in a special event database 314 going forward. The special event database 314 generates the special event specification 303. Each element 316 processed by the data element processor 300 is stored with its appropriate data series at 318. The data series 318 is sometimes referred to below as a processed data series DSi.

Initial Data Load and Ongoing Processing

Figure 4:
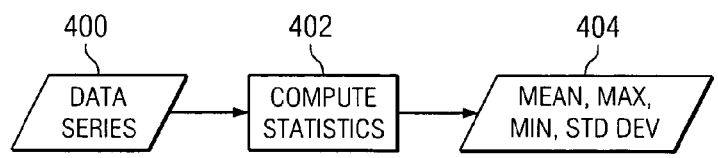
FIG. 4 illustrates a process of computing statistics based on the data series according to an illustrative embodiment of the invention.

The steps of separating/classifying data into data series (FIG. 2) and processing by filtering out exception/special situations (FIG. 3) preferably are performed as new data becomes available to the system through the one or more data collectors (or other means). When data becomes available for an ATM for the first time, it is desirable to load into the system all available data for the ATM and to compute historical statistics. This is illustrated in FIG. 4 for a given data series 400. In this example, a set of statistics (mean, maximum, minimum, standard deviation) 402 is computed by a computation process 404. As needed, data can be processed against the historical statistics for the purposes of exception and special event processing.

Withdrawal Models

With the above as background, the following describes how the forecasting system of the present invention builds a model for the withdrawal data series that is then used for prediction, namely, predicting withdrawal amounts by date, forecasting demand during a period, computing load amounts for a given ATM for given period and confidence level, forecasting residual amounts in current load period for an ATM and optimum load periods and schedules.

Generally, no mathematical function of a given set of factors can fit an observed data series perfectly, i.e., given a modeling function the data series, the difference (actual value−the value computed by the model function) for each of the dates in the data series is not necessarily zero. Thus when a modeling function is defined to represent a data series, one can compute the remaining error corresponding to the each element (date). This leads to an important insight of the present invention, namely, that the variation in the withdrawals may be modeled by two components:

A predictable component that is a function, $f(date)$, and

A random variation component that is not explained by factors represented in the model Modeling Function For given withdrawal data series, such as a processed withdrawals data series for Mondays, one can define a modeling function $f_{monday}(date)$ to model the predictable components of withdrawals. When it is not necessary to distinguish the underlying weekday (the primary identifier of independent data series), the following description will refer to this function simply as $f(date)$.

According to an illustrative embodiment of the invention, this modeling function, $f(date)$, preferably has several different components:

a non-periodic component, a periodic component which itself preferably has one or more components:

continuous or piecewise continuous periodic component, and a quasi-periodic, discrete valued component, a special situation component, and an environmental and other auxiliary factors component.

In one particular embodiment, but without limitation, the modeling function is specified as follows:

$$f(date) = wnp_1*(date) +$$
$$wc12*\cos(2*\pi*date/365) + +ws12*\sin(2*\pi*date/365) +$$
$$wc6*\cos(2*\pi*date/182) + ws6*\sin(2*\pi*date/182) +$$
$$wc3*\cos(2*\pi*date/91) + ws3*\sin(2*\pi*date/91 - ph3) +$$
$$\sum_{i=1,\ldots,4} wm_i * ismonth(date, i) + \sum_{i=1,\ldots,31} wd_i * isday(date, i) +$$
$$\sum_{i=1,\ldots,7} wwd_i * isweekday(date, i) +$$
$$\sum_{i=1,\ldots,4} ww4w_i * iswkin4wkcycle(date, i) +$$
$$w_{payday} ispayday(date) + w_{holiday} isholiday(date) +$$
$$w_{preholiday} ispreholiday(date) + w_{postholiday} ispostholiday(date) +$$
$$\sum_{i=1,\ldots,3} wsnow_i * issnowinrange(date, i) +$$
$$\sum_{i=0,1,\ldots,12} wtemp_i * istempinrange(date, i)$$

The following explains the above-identified modeling function in more detail, first by classifying the various parts of the function into the component categories mentioned earlier. Computation of the parameters of the model is also described.

Modeling Function Components

Non-periodic component:

$$wnp_1*(date)$$

a) This component represents a long term, non-periodic, linear growth (or decline) of withdrawals;

b) Note that this component can be expressed more generally as $wnp_0+wnp_1*(date)$ or $wnp_0+wnp_1*(date)+wnp_1*\log(date)$ and many other such variations, although the fixed component $wnp_0$ can be omitted.

Continuous or piecewise continuous periodic component:

$$wc12*\cos(2*\pi*date/365) + +ws12*\sin(2*\pi*date/365)$$
$$+wc6*\cos(2*\pi*date/182)+ws6*\sin(2*\pi*date/182)$$
$$+wc3*\cos(2*\pi*date/91)+ws3*\sin(2*\pi*date/91-ph3)$$

a) These non-linear, periodic functions model periodic change; the periods for these functions, namely, 365 days, 182 days and 91 days, model the annual, semi-annual and quarterly variations;

b) Other periodic functions, such as Fourier Series, can be used instead of these functions; one such example is a Fourier Series with period P and N-Harmonics is defined as $FSN(x,p)=\Sigma_{i=1,\ldots,N}(a_i*\cos(2*\pi*x/p)+b_i*\sin(2*\pi*x/p))$;

c) The number of periodic components can be increased; further, rather than fixing the periods, the periods can be determined automatically through regression analysis;

d) it is generally not necessary to represent variation within a month using periodic components as, preferably, those are taken into account by the quasi-periodic components below.

Quasi-periodic, discrete valued component:

$$\Sigma_{i=1,\ldots,4} wm_i*ismonth(date,i)$$
$$+\Sigma_{i=1,\ldots,31} wd_i*isday(date,i)$$
$$+\Sigma_{i=1,\ldots,7} wwd_i*isweekday(date,i)$$
$$+\Sigma_{i=1,\ldots,4} ww4w_i*iswkin4wkcycle(date,i)$$

a) Where:

i) ismonth(date,i)=1 if "month for date"=i else 0 ii) isday(date,i)=1 if "day number in the month for date"=i else 0 isweekday(date,i)=1 if "day of the week for date"=i else 0 iv) iswkin4wkcycle(date, i)=1 if "week number for the date in a 28 day (4 week) cycle since a reference date"=i else 0; reference date can be set arbitrarily to Jan. 1, 2000.

b) As an example, for date Mar. 15, 2001, which is a Thursday, the following values are obtained:

i) ismonth(Mar. 15, 2001,3)=1; ismonth(Mar. 15, 2001, i)=0, i≠3.

ii) isday(Mar. 15, 2001,15)=1; isday(Mar. 15, 2001,i)=0, i≠15.
iii) isweekday(Mar. 15, 2001,4)=1; isweekday(Mar. 15, 2001,i)=0, i≠4.
iv) iswkin4wkcycle (Mar. 15, 2001,3)=1; iswkin4wkcycle (Mar. 15, 2001,i)=0, i≠3.

c) Note that each of the above functions provides a Boolean value (0/1); for computational purposes, it is helpful to create a set of corresponding Boolean variables, e.g., $isday_1, \ldots, isday_{31}$, for each date;

d) If withdrawal data has already been separated into separate data series by day of the week, isweekday(date,i) functions are not needed, as the values of these will be the same for all data elements in the series.

Special situation component:

$$w_{payday} \cdot ispayday(date)$$

$$+w_{holiday} \cdot isholiday(date)$$

$$+w_{preholiday} \cdot ispreholiday(date)$$

$$+w_{postholiday} \cdot ispostholiday(date)$$

a) Where:
  i) ispayday(date)=1 if "date is a payday in ATMs locality" else 0; this information can be obtained either from ATM profile or by heuristics, such as pay cycles are bi-monthly ($15^{th}$ and $30^{th}$ or $31^{st}$ or the working day before these if these dates fall on weekends or are holidays);
  ii) isholiday(date)=1 if "date is a holiday in its locality" else 0; this information can be obtained either from ATM profile or by heuristics, such as look up in a global calendar;
  iii) ispreholiday(date)=1 if "date occurs before a holiday in its locality and has significant activity as a result" else 0; an example will be day before Thanksgiving in USA; this information can be obtained either from ATM profile or by heuristics, such as look up in a global calendar.
  iv) ispostholiday(date)=1 if "date occurs after a holiday in its locality and has significant activity as a result" else 0; an example will be a few days after Thanksgiving in USA; this information can be obtained either from ATM profile or by heuristics, such as look up in a global calendar;

b) As an example, for date Mar. 15, 2001, using the above mentioned heuristic for payday:
  i) ispayday(Mar. 15, 2001)=1
  ii) isholiday(Mar. 15, 2001)=0
  iii) ispreholiday(Mar. 15, 2001)=0
  iv) ispostday(Mar. 15, 2001)=0 c) These are common factors, but this list is not exhaustive.

d) These factors can be represented as Boolean variables.

Environmental and other auxiliary factors component:

$$\Sigma_{i=1, \ldots, 3} wsnow_i \cdot issnowinrange(date,i)$$

$$+\Sigma_{i=0, 1, \ldots, 12} wtemp_i \cdot istempinrange(date,i)$$

e) Where:
  i) issnowinrange(date,i)=1 if "snow on the date was in range i" else 0, where the ranges are defined as 1=Light (0"-3"), 2=Moderate (4"-7") and 3=Heavy (8"+)
  ii) istempinrange(date,i)=1 if "temperature on the date was in range i to" else 0, where range(1)=Temp<10, range(2)=11-20, ..., range(11)=101-110 and range(12)=111+; note that one can easily define ranges in a different way.

f) As an example, on Mar. 15, 2001, when there was no snow and day time high temperature was 42 degrees,
  i) issnowinrange(Mar. 15, 2001,1)=1; issnowinrange(Mar. 15, 2001,i)=0, i≠1.
  ii) istempinrange(date,5)=1, istempinrange(date,i)=0, i≠5.

g) Note that these factors, snow and temperature, are merely representative and is not exhaustive or limiting. Preferably, each of the variables, e.g., snow and temperature on the date in the example above, should be such that a forecast of their value can be determined in advance for forecasting purposes; before these factors can be incorporated in the model, historical values of these factors will also need to be gathered either along with the withdrawal data or independently.

h) These factors can also be represented as Boolean variables.

Computing Model Parameters

As can be seen, the modeling function, $f(date)$, is a combination of several sub-functions and variables, weights for each of which (called model parameters) are represented by $w\text{----}_i$, e.g., $wnp_1, wc12, wd_i$. The value on the date of given variables (e.g., amount of snow on date) and the amount of withdrawal, are measured and the value on the date of individual sub-functions (e.g., cos) or derived-variables (e.g., $issnowinrange_i$ or $isday_i$—see discussion below) are derived from date or ATM profile (see below). Preferably, the model parameters are determined by performing non-linear regression on the resulting equations using standard regression techniques and tools. The purpose of the non-linear regression analysis is to compute the values of these parameters such that the standard deviation of the error, or standard error of estimate, is minimized. Thus, for example, the regression step provides:
  i) model parameters: $w\text{----}_i$, e.g., $wnp_1, wc12, wd_i$.
  ii) standard error of estimate (or model) or StdErr In an illustrative embodiment, one could use non-linear regression techniques implemented in a software package, such as the commercially available package NLREG. Other software packages, such as Datafit, employ a similar approach and may be used. The values of these parameters also can be determined using a multi-step analysis method employing functions built into commercial spreadsheet programs such as Microsoft Excel. Several other optimization or search techniques can be employed to determine the values of these parameters. Additional details for carrying out these tasks are provided below.

Regression Details

Several commercially available tools such as NLREG and Datafit are designed specifically for doing regression. These provide both a programming interface that allows these tools to be embedded or called from other programs as well as an interactive interface to facilitate different modeling functions. To use these tools, one needs to: provide the modeling function, provide the data series, identify a command/call function to do regression, get the parameters of the functions, remaining standard error and other regression related outputs, and (in advance of usage or to fine tune processing) change convergence criterion thresholds and other limits, e.g., number of iterations. As an alternative, one can use tools such as Microsoft Excel to do regression analysis by: setting up parameters for regression, providing initial values for these parameters, setting up data in a spreadsheet (date, withdrawal) in two columns, setting up a first column to compute the withdrawal according to the modeling function (of date, withdrawal and parameters); setting up a second column to compute error (modeled withdrawal value-observed value) for each date, setting up a cell to compute root mean square (RMS) of the error, e.g., as square root of sum of the square of error for each date/number of dates analyzed, and then using an Excel optimization function to minimize RMS error while varying parameters.

While it is generally preferable to perform regression for the complete modeling function in one step, this may not be possible due to numerical issues or processing concerns; in such cases the regression may be performed in a set of steps, e.g. first do regression to estimate parameters of the linear component and a first periodic function, compute its parameters, fix those, and repeat the steps above, to compute the parameters of the $2^{nd}$ periodic function, regressing on the remaining error amounts computed.

Although a goal of regression is to determine the values for the parameters of the withdrawal modeling function $f1$ (date) that provide a low value of standard error, generally it is important to not overfit a function to data. For example, if there is only data for three (3) months, one does not have data to be able to model variations by specific months, e.g., over 6 months and over 12 months. Further, one does not have withdrawals for each weekday on each day number $(1, \ldots, 31)$ of the month. Thus, in such instance, to produce a reliable model that is usable for forecasting, one can build a combined model for all weekdays by using the overall data series and remove corresponding functions from the modeling function, $f_{alldays}$(date), as follows:

Given 3 months data only (for example):

$$f(\text{date}) = wnp_1 * (\text{date}) +$$
$$ws3 * \cos(2*\pi*\text{date}/91) + ws3 * \sin(2*\pi*\text{date}/91 - ph3) +$$
$$\sum_{i=1,\ldots,31} wd_i * isday(\text{date}, i) + \sum_{i=1,\ldots,7} wwd_i * isweekday(\text{date}, i) +$$
$$\sum_{i=1,\ldots,4} ww4w_i * iswkin4wkcycle(\text{date}, i) +$$
$$w_{payday} ispayday(\text{date}) + w_{holiday} isholiday(\text{date}) +$$
$$w_{preholiday} ispreholiday(\text{date}) + w_{postholiday} ispostholiday(\text{date}) +$$
$$\sum_{i=1,\ldots,3} wsnow_i * issnowinrange(\text{date}, i) +$$
$$\sum_{i=0,1,\ldots,12} wtemp_i * istempinrange(\text{date}, i)$$

Summary—Modeling Function

Figure 5:
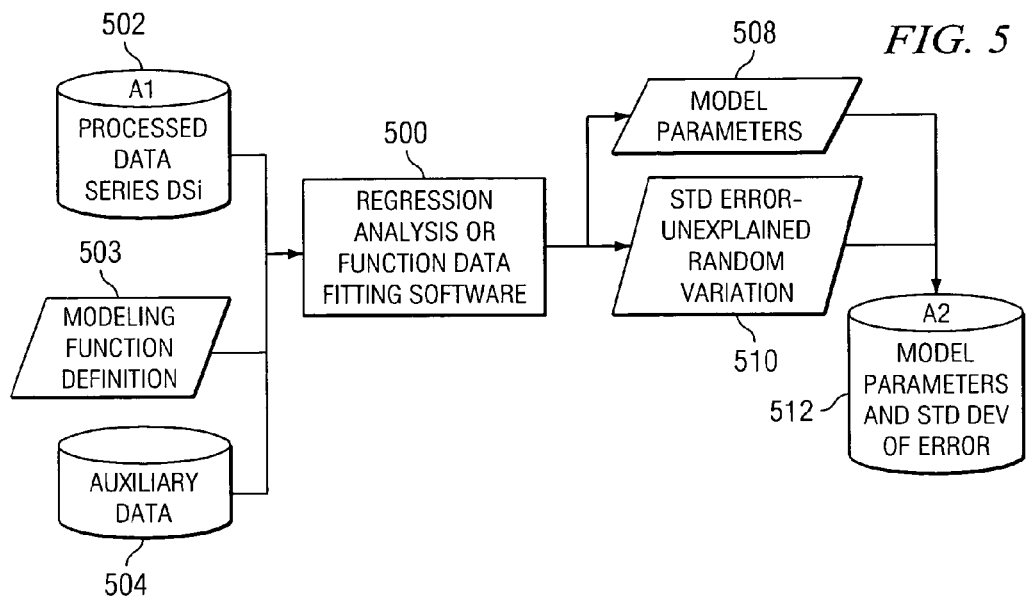
FIG. 5 illustrates a process of building a model for a data series according to the present invention.

Thus, for a given data series, FIG. 5 describes the process of building a model for the data series. The modeling component preferably operates as follows. For each day of the week, the component builds a model of a data series representing cash withdrawals. As noted above, this model preferably is built by single or multiple step non-linear regression analysis containing several components that are represented by linear and non-linear functions and variables, in all cases based on historical withdrawal and auxiliary data.

In particular, a regression analysis or other function data fitting process 500 receives, as inputs: a processed data series DSi 502 (such as generated in FIG. 3), a withdrawal modeling function definition (e.g., $f$(date) above) 502 s and auxiliary data like temperature and snow (if it is available) 504. The outputs of the process 500 preferably comprise model parameters 508 and a standard error for the unexplained random variation 510, which together comprise dataset 512 (the model parameters and standard deviation of residual).

Using Model for Forecasting

The system can now forecast cash demand for each date. In particular, preferably an expected value of the cash withdrawal for a date, Fcst(date), is determined by plugging the date in the model for the day of the week for the date. As an example, using the withdrawal modeling function $f$, if one needs to forecast withdrawals on Sep. 22, 2005, which is a Thursday, then $$Fcst(\text{Sep. 22, 2005}) = f_{Thursday}(\text{Sep. 22, 2005})$$

In addition, given a desired confidence level CL, such as 0.95 or 95%, the system computes an FcstUL "upper limit value" such that the likelihood of withdrawals on that date are less than or equal to the upper limit is given "confidence level" FcstUL(date, CL) as follows:

$$FcstUL(\text{date}, CL) = Fcst(\text{date}) + StdErr_{day\ of\ the\ week}(\text{date}) * Z(CL)$$

where Z is such that $Prob(x \leq Z) = CL$, where x is a random variable with distribution $N(0,1)$, i.e., standard normal distribution.

It should be noted that:

$$Buffer(\text{date}, CL) = FcstUL(\text{date}, CL) - Fcst(\text{date}).$$

Figure 6:
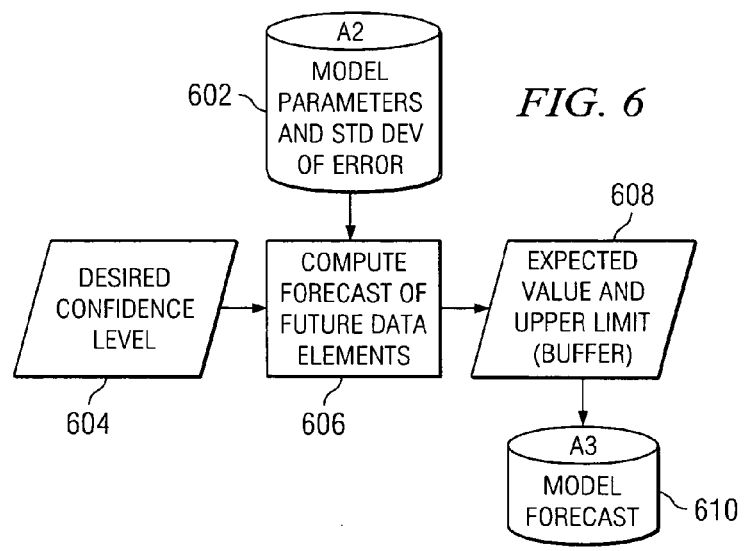
FIG. 6 illustrates a process of forecasting cash demand for a given day according to the present invention.

FIG. 6 illustrates this processing. A dataset 602 (the model parameters and standard deviation of residual (standard error of estimate), as generated in FIG. 5) is applied with the desired confidence level 604 to a computation function 606. An expected value and buffer values 608 are generated and collected as the model forecast 610. Essentially, for each date, the forecasting model generates an initial forecast of expected cash withdrawals. The forecast preferably includes "upper limit" values, or desired values of buffer amount computed as above, to achieve one or more desired confidence levels in the forecast. The forecast of expected withdrawals typically is based on the model for the day of the week, and the unexplained random variation for the day of the week.

While it is possible to re-compute model parameters whenever additional historical data becomes available for an ATM, it is not necessary to do so. One can re-compute the parameters at some regular frequency, e.g., every month and forecast using the existing model, which was updated in not too distant past.

Making Adjustments for Specified Special Event

As discussed above, the ATM system operator may know of one or more events that may occur on specific days that may cause withdrawal demand to be unusually high or low; special events typically are those that are not already incorporated in the modeling function as auxiliary variables. If such special situations have been defined for date, then the initial forecast for the date computed above may be modified to take into account the adjustments defined for the special situation (s). Examples of such adjustments are:

a) Override the expected forecasted value:

Adjusted $Fcst(\text{date}) = $Override value(date)

b) Adjust computed value by specified percentage, Percent_Adjustment:

Adjusted $Fcst(\text{date}) = Fcst(\text{date}) + (1 + $Percent_Adjustment(date)/100)

c) Adjust computed value by specified value, Absolute_Adjustment:

Adjusted $Fcst(\text{date}) = Fcst(\text{date}) + $Absolute_Adjustment (date)

The Fcst and FcstUL values may be updated as follows:

$$Fcst(\text{date}) = \text{Adjusted } Fcst(\text{date}),$$

$$FcstUL(\text{date}) = \text{Buffer}(\text{date}) + Fcst(\text{date}).$$

Figure 7:
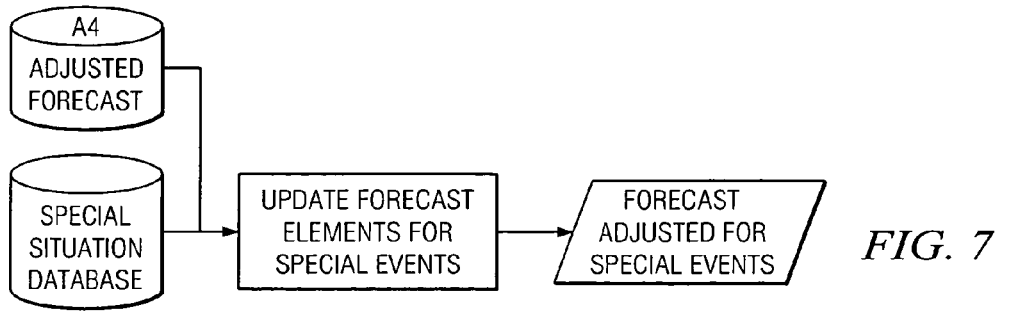
FIG. 7 illustrates a process of updating a forecast to consider special events.

The process is illustrated in FIG. 7.

Forecasting Demand for a Multi-Day Period (Load Period)

For a composite multi-day period of several dates, e.g., a load period, the system can compute a forecast, an expected withdrawal and upper limit on withdrawal for a given confidence level, by aggregating the forecasts for individual dates (FIG. 6 and FIG. 7). Preferably, this aggregation is done using standard statistical techniques of summing up mean and variances of random variables as follows: if there are n days in the composite period, $$CPEV \text{ Composite Period forecast Expected Value} = \sum_{i=\text{dates in the composite period}} EV_i = \sum_{i=\text{dates in the composite period}} Fcst(i)$$

$$CPBF \text{ Composite Period Buffer} = \sum_{i=\text{dates in the composite period}} Bf_i / \sqrt{n} = \left( \sum_{i=\text{dates in the composite period}} Buffer(i) \right) / \sqrt{n}$$

Thus the amount to be loaded or Composite Period Forecast Upper Limit is:

$$CPFcstUL = CPEV + CPBF.$$

Figure 8:
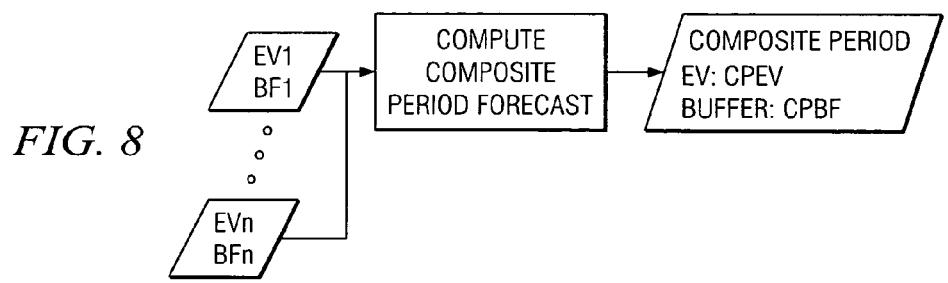
FIG. 8 illustrates a process of generating a forecast for a composite period according to the present invention.

FIG. 8 illustrates one technique for a composite period of n days. In this example, note that EVi=Fcst(i) and Bfi=Buffer (i), and CPBF=Composite Period Buffer.

Adjusting for Bundle Size

Often, the amount to be loaded into an ATM is generally sent as a set of bundles of currency, e.g., $1,000 bundles. Thus, the present invention may adjust load amount to take into account the bundle size, preferably by rounding up to the bundle size the upper limit CPFcstUL computed above. Alternate methods are to round down to the nearest multiple of lower bundle size if the CPFcstUL is very close (say within 10% of bundle size) to the nearest multiple of lower bundle size, otherwise round up to nearest multiple of bundle size.

As an example, if bundle size was $1,000 and CPFcstUL computed above was $21,100, one can round it down to nearest $1,000, which gives CPFcstUL=$21,000. On the other hand, if CPFcstUL computed above was $21,300, it may be desired to round up to the nearest $1,000, which gives CPFcstUL=$22,000. (To keep all numbers consistent, the CPBuffer is appropriately adjusted.)

Taking into Account Machine Capacity

When computing an amount of money to be loaded in a machine during a load period of N days, the CPFcstUL value may be checked against monetary capacity of the machine. If the machine capacity will be exceeded, the operator may be warned, load amount will be changed such that it will be less than or equal to the ATM capacity, and an estimate of the date for which the load is likely to be sufficient will be prepared. Relevant equations are analogous to the ones defined later in the monitoring section and thus are not repeated here for the sake of brevity.

As an example, if the ATM capacity is $40,000 and the calculated load amount for a 14 day period is $41,000, the load amount is reduced to $40,000 and the operator is notified that the load amount is reduced to $40,000, down by $1,000 from the optimum load amount of $41,000 and, that for a given confidence level, it is likely to last for 13 days.

Computing Optimum Load Period Length

A method to compute demand (mean value, required buffer or upper limit for given confidence level CL) for a load period of n days was described above. Given the withdrawal forecast models or functions discussed earlier, the present invention enables one to compute the optimum load period length.

Optimum Load Period Length or optimum number of days between loads preferably is chosen such that per unit cost of loading ATM is a lowest among all feasible (upcoming load date, a subsequent feasible load date) pairs. As an example, given a machine that is loaded on Mondays, with upcoming load date being Jul. 11, 2005, the subsequent load dates will be Jul. 18, 2005, Jul. 25, 2005, Aug. 1, 2005, Aug. 8, 2005, and so on. Thus, a goal here is to identify the load period length out of (for example) 7 days, 14 days, 21 days and 28 days, for which per unit cost of loading the ATM will be lowest.

The following describes a method for computing an optimum number of days between loads by identifying four parts of the solution:

Cost of Loading in a load period
Per Unit Cost of Loading
Computing optimum load period for given load date
Computing optimum load period length over a longer duration in which multiple loads will occur Cost of Loading in a Load Period A total cost to load an ATM during a load period, TCTL, typically consists of multiple factors including, without limitation:

Courier_Cost: cost of sending a courier to the ATM, typically $75/load;
Cost of borrowing money to load into the ATM, which cost itself typically is affected by:
Interest rate (DIR, daily interest rate=Yearly interest rate/365);
Number of days money is borrowed, which itself has one or more parts:
UTD: Number of days Upfront for money to Transit from Bank to the ATM (number of days between borrowing the money and it becoming available in the ATM for withdrawals);
WDD: WithDrawal Day number in the ATM; for the money that gets withdrawn on the day of the load WDD=1;
CBD: Number of days from money being withdrawn from ATM and the money being credited back to the ATM operator's account, typically 1 day;
Amount of money borrowed (and not just withdrawn): for the first day in the load period, this is a total amount for the load period and then the value successively goes down every day as money gets withdrawn; for load period of length k days beginning on ld_date, let:
LA(ld_date,k) (or LA)=Load Amount, CPFcstUL computed above,
W(ld_date+d−1) (or W(d))=Amount expected to be withdrawn on day d, d=1, . . . , k during the load period=Fcst(date)=Fcst(Load_date+d−1);
TMD(ld_date,k)(or TMD): Total Money Dispensed; note that TMD(ld_date,k)=$\Sigma_{d=1, \ldots, k} W(d)$
Residual(ld_date,k) (or Residual)=Amount money expected to be left over at the end of the load period, CPBF computed above; note that Residual=LA−TMD Then, the total cost of loading for k days beginning on date ld_date:

$$TCTL(ld\_date,k) = Courier\_Cost + DIR*(LA*(UTD + CBD) + (\Sigma_{d=1,\ldots,k}W(d)*d) + k*Residual)$$

A computationally simpler approximation gives:

$$TCTL(ld\_date,k) = Courier\_Cost + DIR*(LA*(UTD + CBD) + TMD*(k+1)/2 + k*Residual)$$

Per Unit Cost of Loading

A withdrawal transaction is a natural unit for an ATM, and cost of money per transaction is an important measure in ATM industry. Given average amount of money withdrawn per transaction, AWD, the number of transactions in a load period is then:

$$NT(ld\_date,k) = TMD(ld\_date,k)/AWD$$

If AWD is not available, one can assume AWD=100.

Thus, per unit cost of loading during a load period of k days beginning on ld_date is:

$$PUC(ld\_date,k) = TCTL(ld\_date,k)/NT(ld\_date,k)$$

Figure 9:
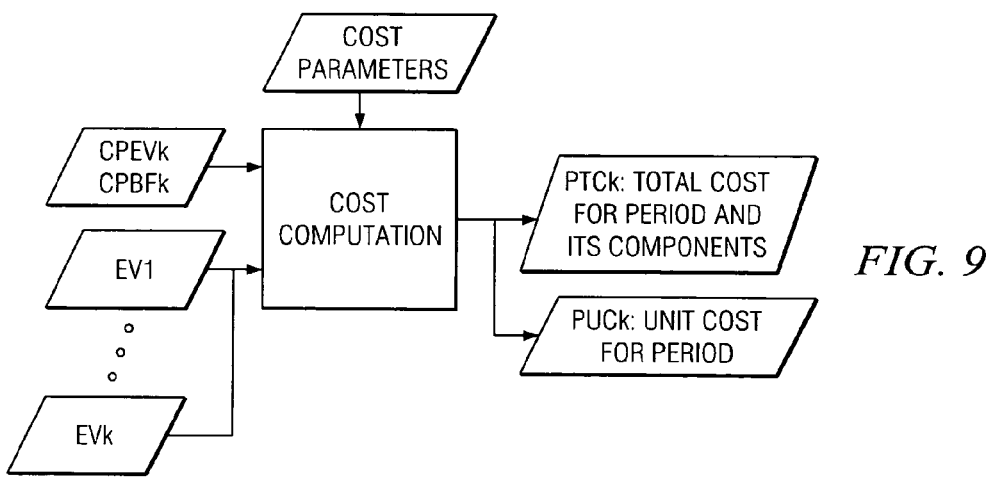
FIG. 9 illustrates a process of computing cost for a load period according to the present invention.

FIG. 9 shows the process of computing cost for a load period of k days in an illustrative embodiment.

Computing Optimum Load Period Length Given a Load Date

Note that as the load period length k increases, TCTL (ld_date,k) increases monotonically but PUC(ld_date,k) does not. PUC first decreases as the courier cost is amortized over a larger number of transactions, and it then increases as the interest cost per transaction keeps increasing, because the money is held for a longer period and the amount of buffer or residual keeps increasing.

To compute the optimum load length given the scheduling constraints, the invention finds k such that per unit cost PUC (ld_date,k) is the lowest among feasible load days, preferably, using following procedure:

1) Set upcoming load date, ld_date; Set j=0
2) Set j=j+1
3) Given scheduling constraints, identify $j^{th}$ feasible next load date, nld_date (for example, because of courier schedules, if the ATM is generally scheduled to be loaded only on Wednesdays, then $j^{th}$ nld_date is $j^{th}$ Wednesday following ld_date).
4) k(j)=nld_date−ld_date
5) Compute PUC(ld_date, k(j)) as shown earlier
6) If {(PUC(ld_date, k(j))<PUC(ld_date, k(j−1))) AND (LA(ld_date,k(j))≦ATM_Capacity)}then {go to step 2 to try longer load period} Else {optimum load period length n=nld_date−ld_date}.

As an example, if the PUC were as follows for load period beginning Jul. 11, 2005:

| Next Feasible Load Date | k (# days in load period) | PUC ($/$100 dispensed) |
|---|---|---|
| Jul. 18, 2005 | 7 | 0.42 |
| Jul. 25, 2005 | 14 | 0.40 |
| Aug. 1, 2005 | 21 | 0.41 |
| Aug. 8, 2005 | 28 | 0.48 |

The algorithm chooses load period of 14 days, with subsequent load being on Jul. 25, 2005.

Figure 10:
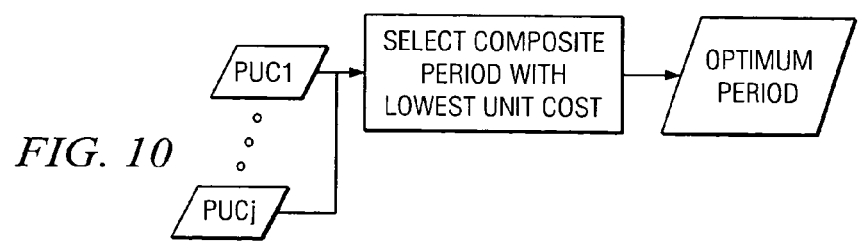
FIG. 10 illustrates a process of determining optimum load period length that minimizes per unit cost according to the present invention.

The process is illustrated in FIG. 10.

Computing Optimum Load Period Length Given a Period During which Multiple Loads Will Occur and Scheduling Constraints Often, an ATM operator needs to tell the courier a month or more in advance the load schedule for each ATM. The present invention achieves this goal as follows:

1) Given starting date for establishing the new schedule, start with the first load date and successively compute optimum load period length for it and the next load date;
2) If a fixed load period length is desired, then, take an average of the load period lengths obtained in step 1 above, and if the load can occur only at certain frequency, round it up or down to closest feasible frequency (e.g., 1 week, 2 weeks, and so on).
3) If it is possible to change the weekday of the load, pick the day before the weekdays that has a highest average withdrawal.

Monitoring to Prevent Runouts in the Current Load Period

Once an ATM has been loaded with money, the system preferably monitors it on an on-going basis. When data for withdrawal on date "date" arrives, preferably, the system not only checks it for exceptions, but also determines the remaining balance in the ATM and whether it will be sufficient to support withdrawals in the remaining part of the current load period.

The invention uses the forecast information computed when the load amount was determined and recent withdrawal information to estimate the remaining balance in the ATM and its sufficiency.

Let:
currlddate: Load date for the current load period
N: the length of the current load period
lwdate: date for which the latest withdrawal data just arrived;
L: the number of remaining days in the current load period;
P: the number of days already past in the current load period; therefore, the dates for the days in the load period that are already past are currlddate, . . . currlddate+P−1;
WD(d): the amount withdrawn on date d;
EODBAL(d): remaining balance in ATM at the end of the date d;
PDAct: Actual withdrawals during past days of the current load period;
PDFcst: Expected value of forecasted withdrawals during past days of the current load period;
PDFcstUL: Expected upper limit on forecasted withdrawals during past days in the current load period;
Fcst(d): Forecasted expected value (mean) of amount of withdrawals on the date d;
FcstUL(d)): Forecasted Upper Limit on amount of withdrawals on the date d;
RDFcst: Expected value of forecasted withdrawals during remaining days of the current load period;
RDFcstUL: Given confidence level, Upper Limit on forecasted withdrawals during remaining days in the current load period;
RResidualEV: Revised estimate of the Expected Value of Residual at the end of this load period
RResidualLL: Revised estimate of the Lower Limit of Residual at the end of this load period at given confidence level Procedure 1) estimate remaining balance in ATM at the end of lwdate, $$EODBAL(lwdate) = EODBAL(lwdate-1) - WD(lwdate),$$

2) compute withdrawal statistics in current load period from ATM by the end of lwdate, $$PDAct = \Sigma_{p=1,\ldots,P}W(currlddate+p-1)$$

$$PDFcst = \Sigma_{p=1,\ldots,P}Fcst(currlddate+p-1)$$

$$PDFcstUL = PDFcst + (\Sigma_{p=1,\ldots,P}FcstUL(currlddate+p-1) - PDFcst)/\sqrt{P}$$

3) determine if a potential exception or special event has occurred by comparing the amount withdrawn against the withdrawal forecasted and notifies the operator, e.g., If($WD(lwdate) > FcstUL(lwdate)$)then Notify "Withdrawals on ATM on lwdate Are Much Larger Than Expected"

4) determine when the ATM is likely to run out of money, preferably, as follows:
a) Compute demand for the remaining days in the current period $RDFcst = \Sum_{l=1,\ldots,L} Fcst(lwdate+l)$ $RDFcstUL = RDFcst + (\Sum_{l=1,\ldots,L} FcstUL(lwdate+l) - RDFcst)/\sqrt{L}$ b) Adjust it for the recent experience, if so desired, e.g.,

```
If (PDFcstUL < PDAct) then {
    RDFcst = RDFcst * PDAct/PDFcstUL
    RDFcstUL = RDFcst * PDAct/PDFcstUL
}
``` c) Compute expected residuals:

$RResidualEV = EODBAL(lwdate) - RDFcst$ $RResidualLL = EODBAL(lwdate) - RDFcstUL$ d) determine a date that the system would expect the remaining money to last with a given confidence level:

```
If (RResidualLL < 0) {
/* ATM does not have enough money left to meet the upper limit on
demand */
/* Find k, number of days up to which the remaining amount will be
sufficient */
Find k, k between 0 and L-1, such that estimated Lower Limit on
Residual after k days is >= 0 and is <0 on k+1 day, where
    kDFcst = Σ_{l=1,...,k} Fcst(lwdate+l)
    kDFcstUL = kDFcst + (Σ_{l=1,...,k} FcstUL(lwdate+l) - kDFcst)/√k
    If (PDFcstUL < PDAct) then {
        kDFcst = kDFcst * PDAct/PDFcstUL
        kDFcstUL = kDFcst * PDAct/PDFcstUL
    }
    kResidualEV = EODBAL(lwdate) - kDFcst
    kResidualLL = EODBAL(lwdate) - kDFcstUL
    /* Note that this computation was already done for k=L and the desired
    value can be done simply by first computing the above for k=L-1
    and keep decreasing k until the condition is met. */
}
Else {
/* ATM has enough money left to meet the upper limit on demand */
/* Find k, number of days up to which the remaining amount will be
sufficient */
Find k, k ≧ L, such that estimated Lower Limit on Residual after k days
is >= 0 and is <0 on k+1 day where:
    kDFcst = Σ_{l=1,...,k} Fcst(lwdate+l)
    kDFcstUL = kDFcst + (Σ_{l=1,...,k} FcstUL(lwdate+l) - kDFcst)/√k
    If (PDFcstUL < PDAct) then {
        kDFcst = kDFcst * PDAct/PDFcstUL
        kDFcstUL = kDFcst * PDAct/PDFcstUL
    }
    kResidualEV = EODBAL(lwdate) - kDFcst
    kResidualLL = EODBAL(lwdate) - kDFcstUL
    /* Note that this computation was already done for k=L and the desired
    value can be done simply by first computing the above for k=L+1
    and keep increasing k until the condition is met. */
}
```

5) Notify user of the EODBAL, expected value of additional withdrawals till the end of the current load period (RDFcst), upper limit on additional withdrawals till the end of the current load period (RDFcstUL), and estimate of the date on which there is a possibility that the machine can run out, date+k, Once the analysis has been done on a given (e.g., recent) arrival of withdrawal data, the operator can make a mid-course correction, e.g., 1) Compute an emergency load amount and order an ATM load; and/or
2) Delay a next planned load.

Variants

The following section describes some of the other capabilities or variations that may be included in the inventive system:

Dealing with Multiple Denominations

The following approaches may be used:
a) Build separate model for each denomination, or
b) Build model for the aggregate amount and a relative distribution of different denominations.

Dealing with Add/Swap

Further, if the loading process requires that the load amount is added to the money that may already be present in the ATM at the loading time, rather than swapped with the money remaining in the ATM at the time of load, the system can adjust the load amount to take into account the expected minimum value of the money already expected to be in the ATM when the load is performed. An illustrative way to do make the adjustment is as follows:

estimate mean and standard deviation of the random variable corresponding to the amount remaining in the ATM at the load time using similar computations (see monitoring steps described earlier), define a new random variable (r.v.) corresponding to required amount to be loaded=r.v. representing withdrawals during the composite period−r.v. corresponding to the amount remaining in the ATM at the load time, estimate mean and variance of this new random variable using the standard statistical techniques, compute required buffer and upper limit for this random variable.

This now gives an adjusted load amount CPFcstUL.

It should also be noted that the there is no other additional "Transit Time" for this money and the interest cost of this money is appropriately computed.

Recycling of the Deposited Money

It may also be desirable to forecast as a function with respect to recycling of the money that has been deposited by a customer in an ATM. In this alternative, the system forecasts the expected value of the money to be deposited instead of an upper limit and lower limit (for given confidence level) of the money to be deposited. The system may further forecast the expected value of the recyclable money instead of upper limit, lower limit (for given confidence level) of the recyclable money. Preferably, the system also monitors this amount on a given, periodic basis. Load size may also be reduced appropriately as the interest rate for the recycled money may be different from the non-recycled or borrowed money.

Managing a Multi-ATM Site

This system and method are easily adapted to manage a multi-ATM site. For example, one can construct the data series for the entire ATM site by simply adding the withdrawals for each of the ATMs for every day to obtain total withdrawals at the site. The remaining balance at each of the ATMs can also be accumulated and used in the forecasting process. A prediction then is done for the total site in the manner previously described. The load amounts are then distributed to individual ATMs in proportion to their capacity.

Computing Optimum Confidence Level

Rather than arbitrarily choosing a confidence level, the system can further optimize the loading process to reduce overall cost by taking into account the cost of ATM run out. This cost can be defined, for example, as a minimum of:

Cost of reloading the ATM, which includes emergency courier costs, cost of borrowing money, administrative costs, and the like; this cost can be reduced if a next load can be cancelled and combined with this emergency load, and Cost of not replenishing the ATM, which includes lost revenue in terms of lost transaction fees and loss of goodwill.

Construction of the Modeling Function

One of ordinary skill will appreciate that there are several variations that are easily conceptualized on the modeling function and data aggregation. A few of these are outlined below.

Periodic Functions:

(a) Frequencies may also be automatically determined (b) For each period, higher harmonics for periodic functions are included (as in Fourier series), rather than one cosine and sine function at each period.

$$FSN(x,p)=\Sigma_{i=1,\ldots,N}(a_i*\cos(2*\pi*x/p)+b_i*\sin(2*\pi*x/p))$$

It can be seen that having functions with periods of 1 year, 6 months and 3 months is equivalent to having 3 harmonics of a Fourier Series with period of 1 year.

(c) Cosine or sine functions are included with phase shift, rather than a combination of cosine and sine functions, i.e., a function in the form of $a*\sin(2*\pi*date/pd-ph)$ may be considered equivalent to a function in the form of $wc*\cos(2*\pi*date/pd)+ws*\sin(2*\pi*date/pd)$ Non-Periodic Functions (a) Other non-periodic functions may be included in the modeling function, e.g., log(date).

(b) Rather than having binary valued functions, one can have multi-valued functions for factors.

(c) Additional factors may be added to the function.

Other Ways to Define Data Series

As described above, the incoming withdrawal data was separated into defined independent data series by day of the week. The method applies equally well even in situations where it is appropriate to define data series in a different way, e.g., one may have a different data series, e.g., M-Th (non-Friday weekdays), F, and S-S (weekend), or the like. This alternative approach can reduce computation and storage requirements.

Also, if one is interested in only obtaining forecasts for fixed granularity, such as multiple of weeks, one can create aggregate data series in which each data element contains the sum of withdrawals for constituent days. Individual sub-functions within ƒ(weeknum) have to be appropriately defined.

Predicting at Finer Granularity than Day

If the prediction is required for a finer granularity, say by shift or by hour, one can collect withdrawal data at that granularity and then either:

a) Create data series at this granularity (e.g., by hour) and adjust the modeling function accordingly to include day of the week as a variable, or b) Create data series at day of the week granularity as before and adjust the modeling function to include variable corresponding to desired granularity, e.g., ishour (date, i).

Then, the prediction can be analyzed according to the methods discussed earlier.

A Method of Lowering Standard Error of Estimate for Multi-Day Periods

It is possible that the model for weekly withdrawals (base aggregate period=week) may have relatively less random variation than an aggregate of the models for each day of the week (individual data series), i.e., $$Std\_Err(\text{Weekly Model}) < \text{Standard Error of the Aggregate of Weekday Models}$$

or $$Std\_Err(\text{Weekly Model}) < (\Sigma_{day=Sunday,\ldots,Saturday}(Std\_Err(day))^2)^{1/2}/\sqrt{7}$$

In such event, when forecasting demand for a multi-day period of size≧week, the system can construct a modeling function using weekly withdrawal data series (as discussed earlier) and compare its Standard Error of Estimate to that of an aggregate of the day of the week models and select the one that is better.

The present invention provides numerous advantages over the prior art. It particular, this invention provides a novel method and apparatus for forecasting cash demand for ATM or any other cash dispensing device, reliably developing ATM load schedules and monitoring the funds in the ATM to determine the likelihood of fund depletion before a next load. This invention enables ATM operators to optimize their operations taking into account key variables affecting operation. Examples of such variables include, but are not limited to, the constraints on when machines can be loaded, machine capacity for holding cash in different denominations, acceptable likelihood of cash being run out, interest rates, money transit times, cost of loading cash, and the like. The invention is a self-learning system in that it automatically configures itself from the withdrawal data for each ATM separately.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

While the present invention has been described in the context of a method or process, the present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including optical disks, CD-ROMs, and magnetic-optical disks, read-only memories (ROMs), random access memories (RAMs), magnetic or optical cards, or any type of media suitable for storing electronic instructions, and each coupled to a computer system bus.

While given components of the system have been described separately, one of ordinary skill will appreciate that some of the functions may be combined or shared in given instructions, program sequences, code portions, and the like.

While the above-identified invention has been described in the context of an ATM environment, the invention may be practiced in other types of environments such as, without limitation, any situation where it is desirable or necessary to determine supply requirements for any goods (or services) whose demand varies periodically and randomly in complex ways. Thus, for example, this invention is applicable to any other situation where one needs to determine of supply cash, e.g., the amount of money needed for a teller for a bank. Furthermore, this invention provides a novel method for determining time varying expected value, variation in the value and the limit on the maximum amount of the value for given confidence for any set of metrics derived from physical systems.

In addition to or as an adjunct to the dispenser machines themselves, the invention may be implemented within the context of a distributed computing environment that includes a set of computing-related entities (systems, machines, processes, programs, libraries, functions, or the like) that facilitate or provide the above-described functionality. A representative computer is a client workstation or a network-based server running commodity (e.g., Pentium-class) hardware, an operating system (e.g., Linux, Windows 2000, OS-X, or the like), an application runtime environment (e.g., Java), and a set of applications or processes (e.g., applets, servlets, linkable libraries, native code, or the like, depending on platform) that provides the functionality of a given system of subsystem. Conventional network-based access protocols and techniques (e.g., HTTP, SOAP, RPC, and the like) are supported. The method may be implemented as a standalone product, or as a managed service offering. Moreover, the method may be implemented at a single site, or across a set of locations. All such systems, methods and techniques are within the scope of the present invention.

One of ordinary skill will appreciate that the principles of the present invention have general applicability beyond ATM cash forecasting. Indeed, the techniques described herein are applicable to a broad class of problems where one needs to determine the future behavior on the basis of past behavior and come up with optimum solutions. For ease of explanation, the preferred embodiment of the invention is described in the context of determining future withdrawals at an ATM and optimizing the amount of funds (cash, items representing cash, or the like) to be loaded and load schedule for given parameters.

Having described my invention, what I now claim is set forth in the following claims:

1. Apparatus, comprising:
   a processor;
   computer memory holding computer program instructions executed by the processor to perform a method for monitoring a money dispenser that has been loaded with money, the method comprising:
      receiving a data stream of actual withdrawals from the money dispenser from a start of a current load period;
      comparing the actual withdrawals against a withdrawal forecast for the current load period;
      determining a likelihood of the money dispenser running out of money before an end of the current load period by the following sub-steps:
         computing an upper limit on a demand for withdrawals from the money dispenser during one or more remaining time periods in the current load period; and
         using the computed upper limit on the demand for withdrawals, determining, with a given confidence level, a date through which an amount of money remaining in the money dispenser is expected to last; and
      based on the determination of the likelihood of the money dispenser running out of money, taking a given action.

2. The apparatus as described in claim 1 wherein the given action computes an emergency load amount for the money dispenser.

3. The apparatus as described in claim 1 wherein the given action delays a next planned load of the money dispenser.

4. The apparatus as described in claim 1 wherein the step of determining a likelihood of the money dispenser running out of money also includes the sub-step of adjusting the computed upper limit on the demand based on information about recent withdrawals from the money dispenser.

5. The apparatus as described in claim 1 wherein the step of determining a likelihood of the money dispenser running out of money also includes the sub-step computing a demand for withdrawals from the money dispenser during the one or more remaining time periods.

6. The apparatus as described in claim 1 wherein the step of determining a likelihood of the money dispenser running out of money also includes the sub-step of receiving information about the remaining amount of money in the money dispenser.

7. The apparatus as described in claim 1 wherein the step of determining a likelihood of the money dispenser running out of money also includes the sub-step of computing an average value of the demand for withdrawals from the money dispenser during one or more remaining time periods in the current load period.

8. The apparatus as described in claim 6 wherein the upper limit on a demand for withdrawals from the money dispenser during one or more remaining time periods in the current load period is a function of the average value.

9. Apparatus, comprising:
   a processor;
   computer memory holding computer program instructions executed by the processor to perform a method for monitoring a money dispenser that has been loaded with money, the method comprising:
      receiving a data stream of actual withdrawals from the money dispenser from a start of a current load period;
      determining a likelihood of the money dispenser running out of money before an end of the current load period by the following sub-steps:
         computing an upper limit on a demand for withdrawals from the money dispenser during one or more remaining time periods in the current load period; and
         using the computed upper limit on the demand for withdrawals, determining a probability of an amount of money in the dispenser lasting through the current load period; and
      based on the determination of the likelihood of the money dispenser running out of money, computing an emergency load amount for the money dispenser or delaying a next planned load of the money dispenser.

* * * * *